(12) United States Patent
Li et al.

(10) Patent No.: US 8,600,117 B2
(45) Date of Patent: Dec. 3, 2013

(54) AUTOMATIC MEASUREMENT SYSTEM AND METHOD FOR PLANT FEATURES, AND RECORDING MEDIUM THEREOF

(75) Inventors: Yi-Fang Li, Tainan (TW); Szu-Hsuan Wang, Kaohsiung (TW)

(73) Assignee: Institute for Information Industry, Taipei (TW)

( * ) Notice: Subject to any disclaimer, the term of this patent is extended or adjusted under 35 U.S.C. 154(b) by 929 days.

(21) Appl. No.: 12/634,234

(22) Filed: Dec. 9, 2009

(65) Prior Publication Data
US 2011/0116688 A1 May 19, 2011

(30) Foreign Application Priority Data
Nov. 13, 2009 (TW) ................................ 98138565 A (51) Int. Cl.
*G06K 9/00* (2006.01)
(52) U.S. Cl.
USPC .......................................... 382/110; 382/100
(58) Field of Classification Search
USPC .................................................. 382/100, 110
See application file for complete search history.

(56) References Cited

U.S. PATENT DOCUMENTS

| | | | |
|---|---|---|---|
| 7,278,236 B2 * | 10/2007 | McDonald et al. ......... | 47/1.01 R |
| 7,289,646 B2 * | 10/2007 | Hirahara et al. ............. | 382/110 |
| 7,412,330 B2 * | 8/2008 | Spicer et al. ................. | 702/2 |
| 7,617,057 B2 * | 11/2009 | May et al. .................... | 702/62 |
| 7,807,446 B2 * | 10/2010 | MacIsaac et al. ........... | 435/287.1 |
| 2004/0268445 A1 * | 12/2004 | Carlson et al. ............... | 800/295 |
| 2006/0207172 A1 * | 9/2006 | McDonald et al. ........ | 47/58.1 R |
| 2007/0044445 A1 * | 3/2007 | Spicer et al. ................. | 56/10.1 |
| 2007/0289207 A1 * | 12/2007 | May et al. .................... | 47/17 |
| 2010/0042234 A1 * | 2/2010 | May et al. .................... | 700/90 |
| 2010/0093715 A1 * | 4/2010 | Voeste et al. ................ | 514/229.2 |

FOREIGN PATENT DOCUMENTS

| | | | |
|---|---|---|---|
| GB | 2247948 A | * | 3/1992 |
| JP | 05-017505 | | 3/1993 |
| JP | 07-502408 | | 3/1995 |
| JP | 2004-298069 | | 10/2004 |
| JP | 2005-087042 | | 4/2005 |

* cited by examiner

*Primary Examiner* — Shefali Goradia
(74) *Attorney, Agent, or Firm* — Muncy, Geissler, Olds & Lowe, PLLC (57) ABSTRACT

An automatic measurement system for plant features includes: at least one photographic device, for photographing a plant in a container, so as to generate a top view image and a side view image; and an operation processing device, electrically connected to the photographic devices, and at least including an image processing module and a storage unit. The image processing module analyzes at least one of the top view image and the side view image by using at least one image processing procedure and at least one analysis rule, so as to generate at least one feature data corresponding to appearance features of the plant, and records the at least one feature data in the storage unit.

14 Claims, 11 Drawing Sheets

AUTOMATIC MEASUREMENT SYSTEM AND METHOD FOR PLANT FEATURES, AND RECORDING MEDIUM THEREOF

CROSS-REFERENCE TO RELATED APPLICATION

This application claims the benefit of Taiwan Patent Application No. 098138565, filed on Nov. 13, 2009, which is hereby incorporated by reference for all purposes as if fully set forth herein.

BACKGROUND OF THE INVENTION

1. Field of the Invention

The present invention relates to an automatic measurement system, an automatic measurement method, and a recording medium, and more particularly to an automatic measurement system for plant features, an automatic measurement method for plant features, and a recording medium thereof.

2. Related Art

In recent years, as green environmental protection is strongly advocated, more and more people begin to plant flowers and trees, so as to make the living environment more favorable. For personnel in the field of floriculture, if intending to cultivate the planted plant, the personnel need to periodically track and record some appearance features of the plant during the growth process after seeding, for example, a leaf amount, a leaf length, a width, or a leaf area of the plant, such that the personnel can know whether growth conditions provided by the planting environment is suitable for the plant, or the personnel can use the features for other research purposes.

However, currently, the personnel usually records the plant features by using a ruler, naked eyes, personal experience or other conventional methods, that is to say, the plant features are mostly manually measured and recorded. Therefore, in the modern times with advanced technologies, there is still a space for improvement of the method in which the data of the plant features is not automatically recorded.

SUMMARY OF THE INVENTION

Accordingly, the present invention is directed to an automatic measurement system for plant features, an automatic measurement method for plant features, and a recording medium thereof, so as to solve the above problems.

To achieve the above objectives, the present invention provides an automatic measurement system for plant features, which includes: at least one photographic device, for photographing a plant in a container, so as to generate a top view image and a side view image; and an operation processing device, electrically connected to the photographic devices, and at least including an image processing module and a storage unit. The image processing module analyzes at least one of the top view image and the side view image by using at least one image processing procedure and at least one analysis rule, so as to generate at least one feature data corresponding to appearance features of the plant, and records the at least one feature data in the storage unit.

To achieve the above objectives, the present invention also provides an automatic measurement method for plant features, which is applicable between at least one photographic device and an operation processing device. The operation processing device at least includes a storage unit. The method includes: obtaining a top view image and a side view image of a plant in a container; analyzing at least one of the top view image and the side view image by using at least one image processing procedure and at least one analysis rule, so as to generate at least one feature data corresponding to appearance features of the plant; and recording the at least one feature data in the storage unit.

To achieve the above objectives, the present invention further provides a computer readable recording medium, for storing a computer program. The computer program is readable by an operation processing device to perform an automatic measurement method for plant features. The method is applicable between at least one photographic device and the operation processing device. The operation processing device at least includes a storage unit. The method includes: obtaining a top view image and a side view image of a plant in a container; analyzing at least one of the top view image and the side view image by using at least one image processing procedure and at least one analysis rule, so as to generate at least one feature data corresponding to appearance features of the plant; and recording the at least one feature data in the storage unit.

The efficacy of the present invention lies in that, different from the prior art that the personnel in the field of floriculture record the plant features by using a ruler, naked eyes, personal experience or other conventional methods, in the present invention, by applying the operation processing system and the photographic devices, at least one plant feature photographed by the photographic devices can be digitalized, and the feature data can be automatically recorded in the storage unit, thereby eliminating the inconvenience of having to manually measure and record the plant features.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

In order to make the objectives, features, and advantages of the present invention comprehensible, relevant embodiments of the present invention are described in detail below with reference to the accompanying drawings.

Figure 1A:
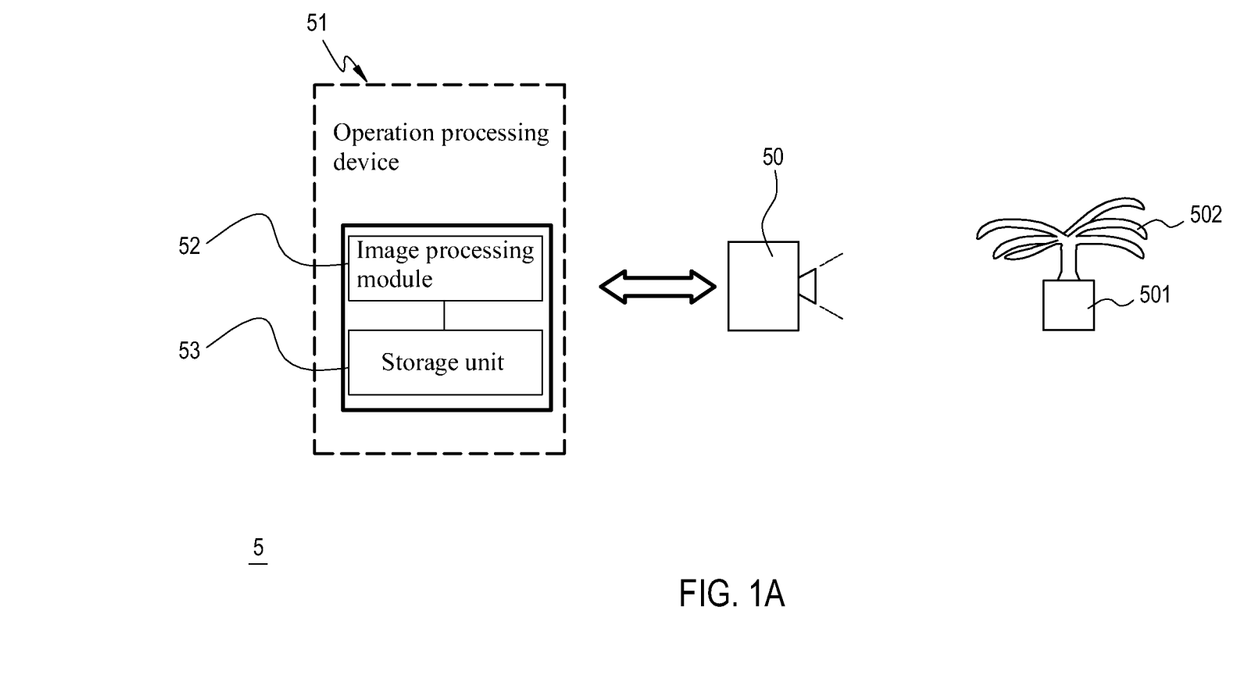
FIG. 1A is a schematic view of an automatic measurement system for plant features according to an embodiment of the present invention.

FIG. 1A is a schematic view of an automatic measurement system for plant features according to an embodiment of the present invention.

Referring to FIG. 1A, the automatic measurement system for plant features 5 includes at least one photographic device 50 and an operation processing device 51. The photographic device 50 may be a camera, a video camera, a digital camera, a digital video (DV), or a like device.

The at least one photographic device 50 is used for photographing a plant 502 of a container 501 so as to generate a top view image and a side view image, thereby fully photographing appearance features of the plant 502 from various angles. The at least one photographic device 50 is capable of photographing the plant 502 in the container 501 and generating the corresponding top view image and side view image. In addition, in order to increase the brightness of the ambient environment when the plant 502 is photographed, the automatic measurement system for plant features 5 further includes a light-emitting unit, for providing a light source, so as to assist the at least one photographic device 50 to photograph the appearance features of the plant 502 in the container 501.

The operation processing device 51 may be implemented by a computer system, an embedded system, or an electronic device having image processing and operating functions. The operation processing device 51 is electrically connected to the at least one photographic device 50 (shown by a double-headed arrow in FIG. 1A). The operation processing device 51 includes an image processing module 52 and a storage unit 53. The image processing module 52 analyzes at least one of the top view image and the side view image by using at least one image processing procedure and at least one analysis rule, so as to generate at least one feature data corresponding to the appearance features of the plant 502.

Further, the operation processing device 51 further generates at least one feature data corresponding to the plant 502 in the container 501 at different times and records the at least one feature data in the storage unit 53, and the at least one analysis rule is used for analyzing the top view image and the side view image corresponding to the different times, so as to generate the at least one feature data corresponding to the appearance features of the plant 502. Moreover, the operation processing device 51 further generates at least one selected from a group consisting of a recording report, a plant growth analysis, and a plant growth history corresponding to the plant 502 in the container 501 according to the at least one feature data corresponding to the plant 502 in the container 501 at the different times by using a plant record processing procedure.

The image processing module 52 records the feature data in the storage unit 53. The feature data includes, for example, a leaf number of the plant 502, a leaf length of the plant 502, a leaf width of the plant 502, a leaf area of the plant 502, a bud number of the plant 502, a sprout number of the plant 502, a height of the plant 502, or an angle between leaves of the plant 502 such as the angle between two leaves in the highest layer of the plant 502.

In addition, the storage unit 53 prestores a dimension data of an object with a fixed dimension. Therefore, by comparing the dimension of the object for calculating the dimension of the plant 502, the actual dimension of the plant 502 can be obtained. The dimension data may be, for example, an actual dimension data of the container or other objects with a fixed dimension. Alternatively, the automatic measurement system for plant features 5 further includes a standard dimension device having a standard dimension marker, and then, the automatic measurement system obtains the actual dimension data of the plant 502 in the container 501 and generates the at least one feature data corresponding to the appearance features of the plant 502 by using the standard dimension marker, the image processing procedure, and the at least one analysis rule.

Figure 1B:
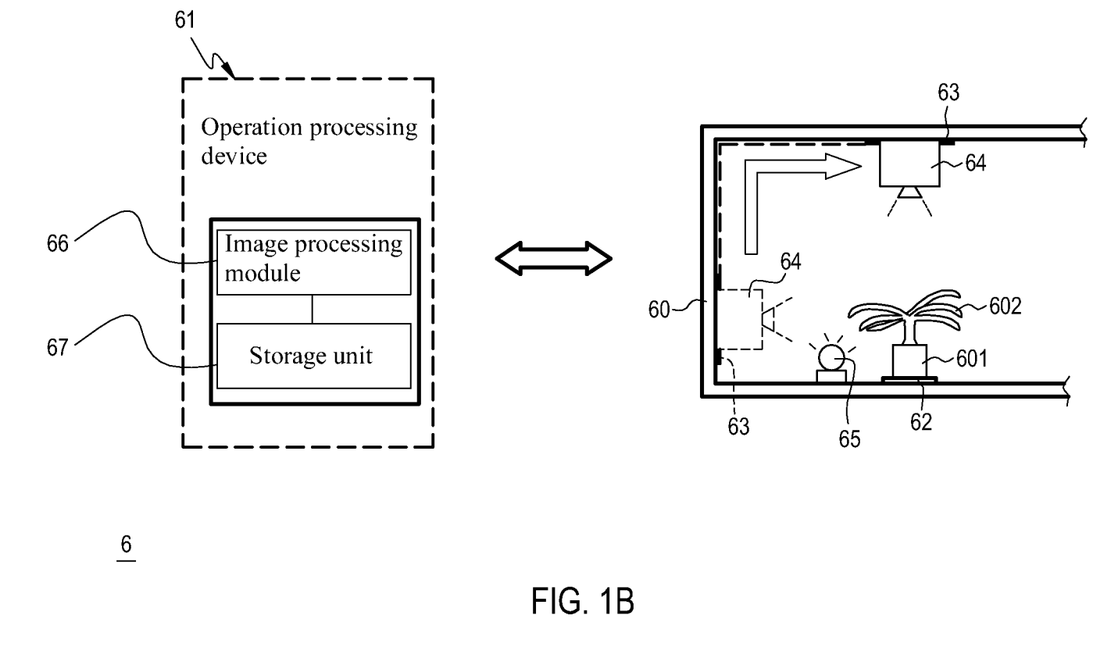
FIG. 1B is a schematic view of an automatic measurement system for plant features according to another embodiment of the present invention.

FIG. 1B is a schematic view of an automatic measurement system for plant features according to another embodiment of the present invention.

Referring to FIG. 1B, the automatic measurement system for plant features 6 includes a supporting mechanism 60, at least one photographic device, and an operation processing device 61.

The supporting mechanism 60 includes a positioning mechanism 62 and a moving mechanism 63. The positioning mechanism 62 is used for positioning a container 601 on the supporting mechanism 60. Here, the at least one photographic device is implemented by a first photographic device 64. The moving mechanism 63 is an automatic moving mechanism. The moving mechanism 63 is capable of moving above and beside the container 601 along a frame rail of the supporting mechanism 60, such that the first photographic device 64 disposed on the moving mechanism 63 can photograph a plant 602 in the container 601 so as to generate a top view image and a side view image, or can be used in combination with a pivoting lens of the first photographic device 64 to photograph the plant 602 in the container 601 so as to generate a top view image and a side view image.

In addition, in order to increase the brightness of the ambient environment when the plant 602 is photographed, the automatic measurement system for plant features 6 further includes a light-emitting unit 65, for providing a light source, so as to assist the first photographic device 64 to photograph the appearance features of the plant 602 in the container 601.

The operation processing device 61 may be implemented by a computer system, an embedded system, or an electronic device having image processing and operating functions. The operation processing device 61 has the same functions as the operation processing device 51 described above, and includes an image processing module 66 and a storage unit 67, and the details will not be described herein again.

Figure 1C:
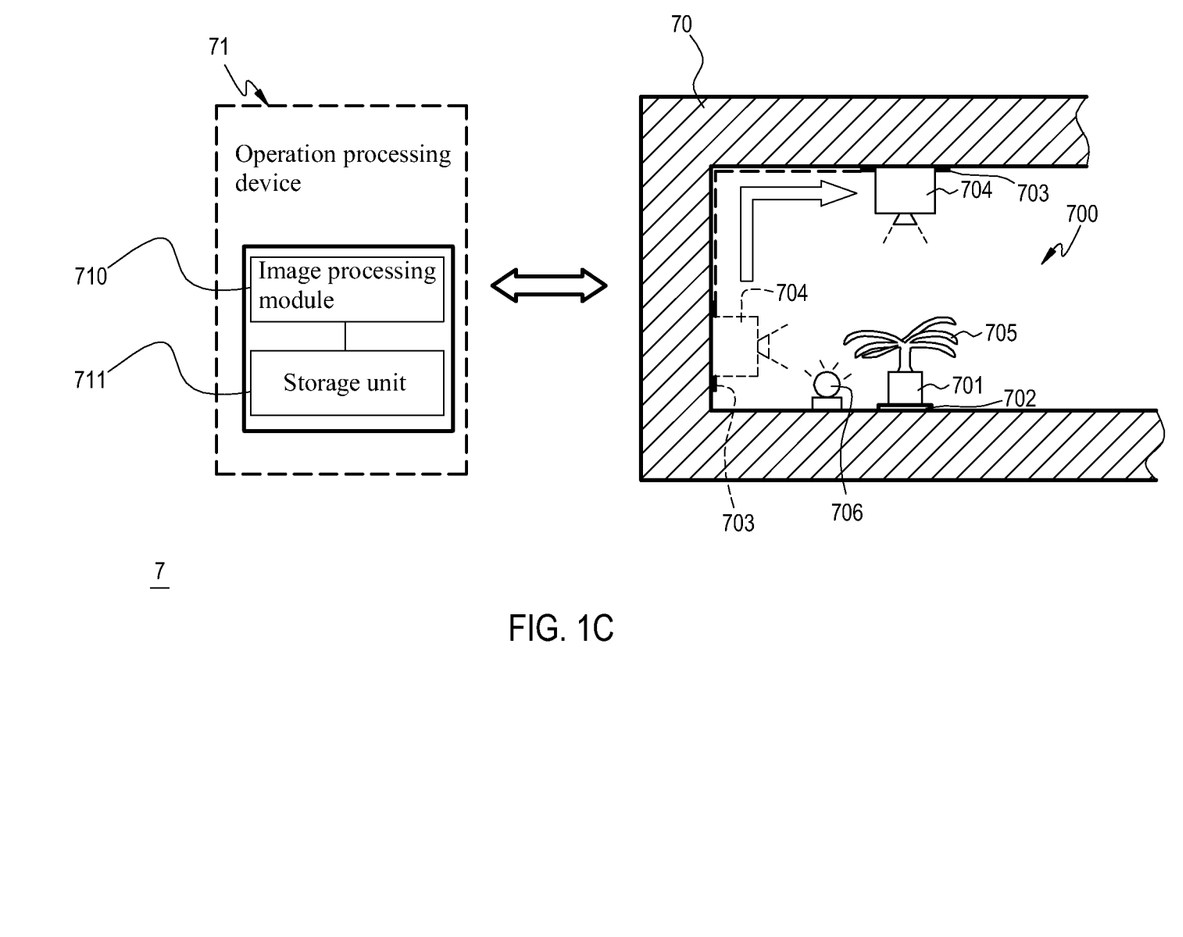
FIG. 1C is a schematic view of an automatic measurement system for plant features according to another embodiment of the present invention.

FIG. 1C is a schematic view of an automatic measurement system for plant features according to another embodiment of the present invention.

Referring to FIG. 1C, the automatic measurement system for plant features 7 includes a case 70, at least one photographic device, and an operation processing device 71.

The case 70 has a chamber 700 for placing a container 701 therein such that the container 701 is positioned in the case 70. The case 70 includes a positioning mechanism 702 and a moving mechanism 703. The positioning mechanism 702 is used for positioning the container 701 in the case 70. Here, the at least one photographic device is implemented by a first photographic device 704 (for example, a video or photographic photographic device). The moving mechanism 703 is an automatic moving mechanism disposed in the case 70. The moving mechanism 703 is capable of moving above and beside the container 701 along a frame rail of the case 70, such that the first photographic device 704 disposed on the moving mechanism 703 can photograph a plant 705 in the container 701 so as to generate a top view image and a side view image, or can be used in combination with a pivoting lens of the first photographic device 704 to photograph the plant 705 in the container 701 so as to generate a top view image and a side view image.

In addition, in order to increase the brightness of the ambient environment when the plant 705 is photographed, the automatic measurement system for plant features 7 further includes a light-emitting unit 706, for providing a light source, so as to assist the first photographic device 704 to photograph the appearance features of the plant 705 in the container 701.

The operation processing device 71 may be implemented by a computer system, an embedded system, or an electronic device having image processing and operating functions. The operation processing device 71 has the same functions as the operation processing device 51 described above, and includes an image processing module 710 and a storage unit 711, and the details will not be described herein again.

Figure 1D:
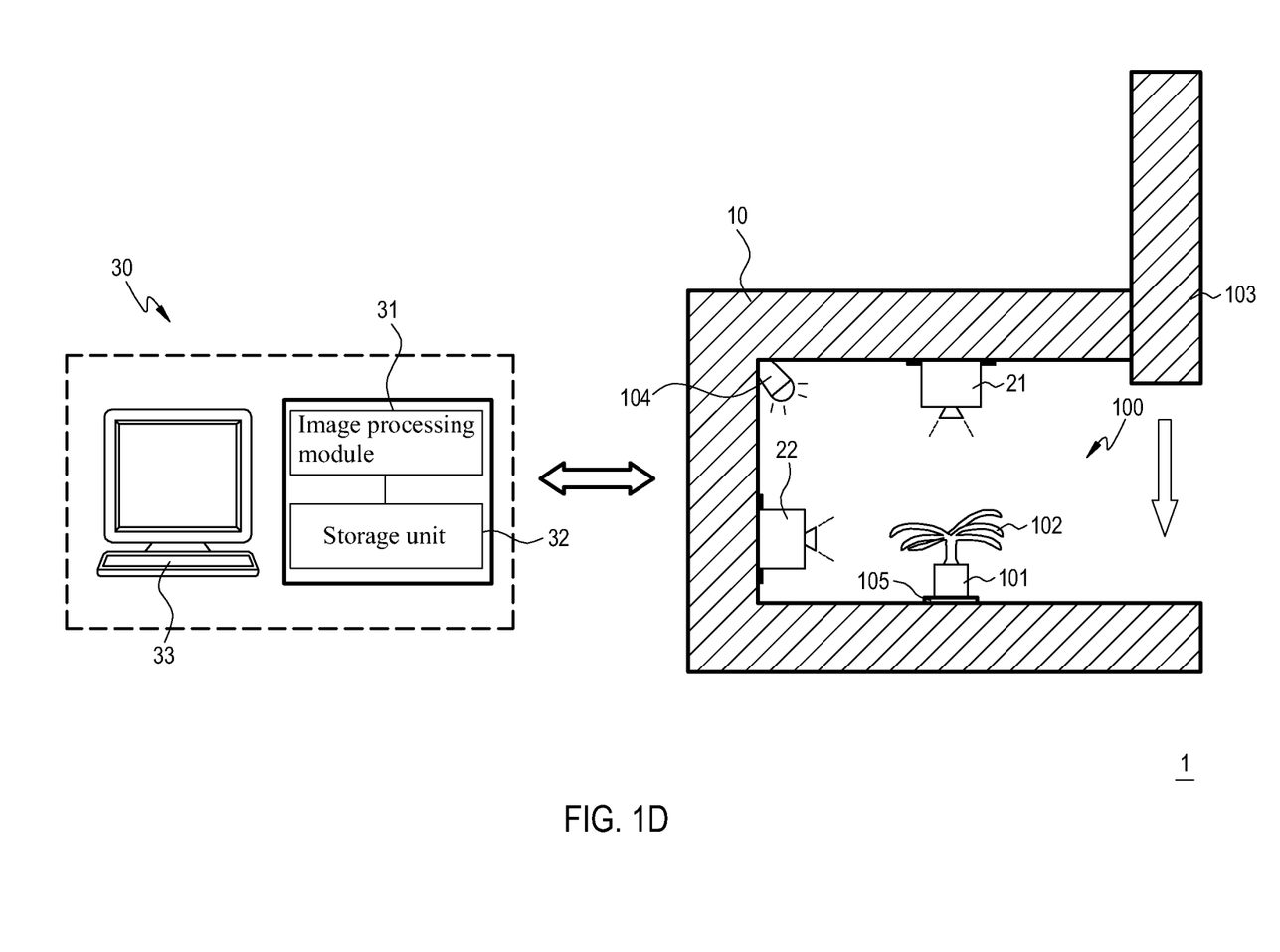
FIG. 1D is a schematic view of an automatic measurement system for plant features according to another embodiment of the present invention.

FIG. 1D is a schematic view of an automatic measurement system for plant features according to another embodiment of the present invention.

Referring to FIG. 1D, the automatic measurement system for plant features 1 includes a case 10, at least one photographic device, and an operation processing device 30.

The case 10 has a chamber 100 for placing a container 101 therein such that the container 101 is positioned in the case 10. The at least one photographic device is implemented by a first photographic device 21 and a second photographic device 22 (for example, video or photographic photographic devices) disposed in the case 10, but the number of the photographic devices is not limited thereto. The first photographic device 21 and the second photographic device 22 are respectively disposed above and beside the container 101, and used for photographing a plant 102 of the container 101 so as to generate a top view image and a side view image, thereby fully photographing appearance features of the plant 102 from various angles.

In addition, the case 10 has a movable door 103 disposed thereon. For the convenience of understanding, the movable door 103 is vertically movable in FIG. 1D. When the movable door 103 is lifted upwards, the chamber 100 is vented to outside, such that a user can place the container 101 in or remove the container 101 from the case 10. When the movable door 103 is closed downwards, the chamber 100 becomes an enclosed space, such that the plant in the case 10 is not affected by external factors (for example, dust or impurities) during the growth process. The case 10 further has at least one light-emitting unit 104 disposed on an inner surface thereof, for providing a light source for the chamber 100. The light source can assist the first photographic device 21 and the second photographic device 22 to photograph the top view image and the side view image of the plant 102 of the container 101.

The case 10 further has a positioning mechanism 105 disposed therein for fixing the container 101, or a position mark can be set on a surface in the case 10 for placing the container 101. The position mark as a reference position is used to make the plant 102 on a fixed position for photographing by the first photographic device 21 and the second photographic device 22.

The operation processing device 30 may be implemented by a computer system, an embedded system, or an electronic device having image processing and operating functions. The operation processing device 30 is electrically connected to the first photographic device 21, the second photographic device 22, and the light-emitting unit 104 (shown by a double-headed arrow in FIG. 1D). The operation processing device 30 has a control unit 33 or a control button for controlling the first photographic device 21, the second photographic device 22, and the light-emitting unit 104. The operation processing device 30 includes an image processing module 31 and a storage unit 32. The image processing module 31 analyzes at least one of the top view image and the side view image by using at least one image processing procedure and at least one analysis rule, so as to generate at least one feature data corresponding to the appearance features of the plant 102, and the image processing module 31 records the feature data in the storage unit 32. The feature data includes, for example, a leaf number of the plant 102, a leaf length of the plant 102, a leaf width of the plant 102, a leaf area of the plant 102, a bud number of the plant 102, a sprout number of the plant 102, a height of the plant 102, or an angle between leaves of the plant 102. In addition, the storage unit 32 prestores a dimension data of an object with a fixed dimension for comparison, based on which an actual dimension of the plant 102 is measured. The dimension data may be, for example, an actual dimension data of the container or other objects with a fixed dimension that are placed in the photographing range. Alternatively, the automatic measurement system for plant features 1 further includes a standard dimension device having a standard dimension marker, and obtains the actual dimension data of the plant 102 in the container 101 and generates the at least one feature data corresponding to the appearance features of the plant 102 by using the standard dimension marker, the image processing procedure, and the at least one analysis rule, which will be described below.

Figure 2:
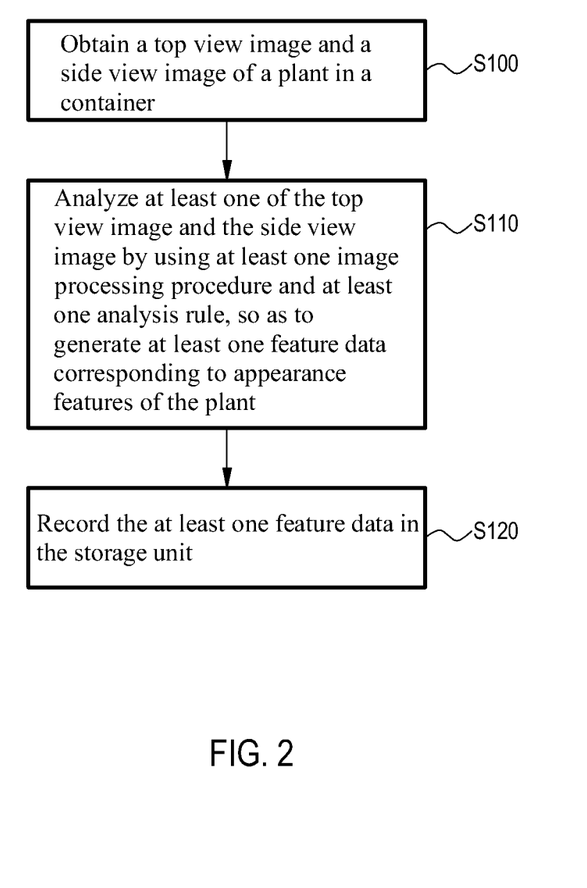
FIG. 2 is a flow chart of an automatic measurement method for plant features according to an embodiment of the present invention.

FIG. 2 is a flow chart of an automatic measurement method for plant features according to an embodiment of the present invention.

Referring to FIG. 2, the automatic measurement method for plant features is applicable between at least one photographic device and an operation processing device, the operation processing device at least includes a storage unit, and the automatic measurement method for plant features includes the following steps.

In Step S100, a top view image and a side view image of a plant in a container are obtained.

In Step S110, at least one of the top view image and the side view image is analyzed by using at least one image processing procedure and at least one analysis rule, so as to generate at least one feature data corresponding to appearance features of the plant.

In Step S120, the at least one feature data is recorded in the storage unit.

For the convenience of understanding, the automatic measurement method for plant features is described below with reference to the automatic measurement system for plant features 1 of FIG. 1D; however, it should be understood that, the present invention is not limited thereto, and the automatic measurement method for plant features is also applicable to any one of the automatic measurement systems for plant features of FIGS. 1A-1C.

Firstly, the Step S100 of obtaining the top view image and the side view image of the plant in the container is performed.

In this step, a user can provide the case 10 and the light-emitting unit 104. The case 10 has the chamber 100 for accommodating the container 101 and the plant 102. The at least one photographic device is implemented by the first photographic device 21 and the second photographic device 22 disposed in the case 10. The first photographic device 21 and the second photographic device 22 are disposed in the case 10 so as to photograph the plant 102 in the container 101. The first photographic device 21 and the second photographic device 22 are respectively disposed in the case 10 and located above and beside the container 101.

The user controls operations of the light-emitting unit 104, the first photographic device 21, and the second photographic device 22 through the control unit 33. That is to say, when the movable door 103 is closed downwards by the user, the light-emitting unit 104 is started by a control signal from the control unit 33 to provide the light source for the chamber 100. At the same time, the first photographic device 21 and the second photographic device 22 disposed above and beside the container 101 begin to photograph the plant 102 in the container 101, so as to generate the top view image and the side view image. Then, the first photographic device 21 and the second photographic device 22 transmit the generated top view image and side view image to the image processing module 31 of the operation processing device 30 for image processing.

Next, the following step is performed: analyzing at least one of the top view image and the side view image by using at least one image processing procedure and at least one analysis rule, so as to generate at least one feature data corresponding to the appearance features of the plant (Step S110).

After receiving the top view image and the side view image, the image processing module 31 of the operation processing device 30 analyzes at least one of the top view image and the side view image by using at least one image processing procedure and at least one analysis rule, so as to generate at least one feature data corresponding to the appearance features of the plant 102.

The image processing procedure includes gray scaling and binarizing at least one of the top view image and the side view image. For example, the top view image or the side view image is converted into a 256-level gray scale image, or both the top view image and the side view image are converted into 256-level gray scale images. That is to say, the image processing module 31 captures a red-green-blue (RGB) value of each pixel in the top view image and the side view image by using the image processing procedure, and then sets the RGB value of each pixel to (R+G+B)/3, so as to obtain 0-255 gray scale images.

Next, if the image processing module 31 intends to binarize the top view image or the side view image (black-and-white image), the image processing module 31 determines a threshold value for the gray scaled image, such that pixels below the threshold value are set to black, and pixels above the threshold value are set to white. For example, the plant 102 and the container 101 can be binarized by using a threshold value of 190.

Then, the image processing module 31 performs a processing operation on the gray scaled and binarized top view image or the gray scaled and binarized side view image according to at least one analysis rule, so as to calculate the feature data corresponding to the appearance features of the plant 102 in the top view image or the side view image. The at least one analysis rule includes at least one selected from a group consisting of a denoising algorithm, an edge algorithm, a shape description algorithm (Chain Code), and a circle detection algorithm.

For example, the denoising algorithm is performed on the binarized top view image or the binarized side view image. The denoising algorithm is capable of scanning each pixel of the binarized top view image or the binarized side view image by using a 3×3 mask, so as to check a relation between a central pixel and peripheral pixels. If the peripheral pixels of the mask include more white pixels than black pixels, the central point is changed to black; and if the peripheral pixels of the mask include more black pixels than white pixels, the central point is changed to white. As such, image noises are smoothed, thereby ensuring that a complete appearance feature image of the plant 102 in the top view image or the side view image is obtained. This part is within the technical scope that can be understood by persons skilled in the art, so the details will not be described herein again.

Figure 3A:
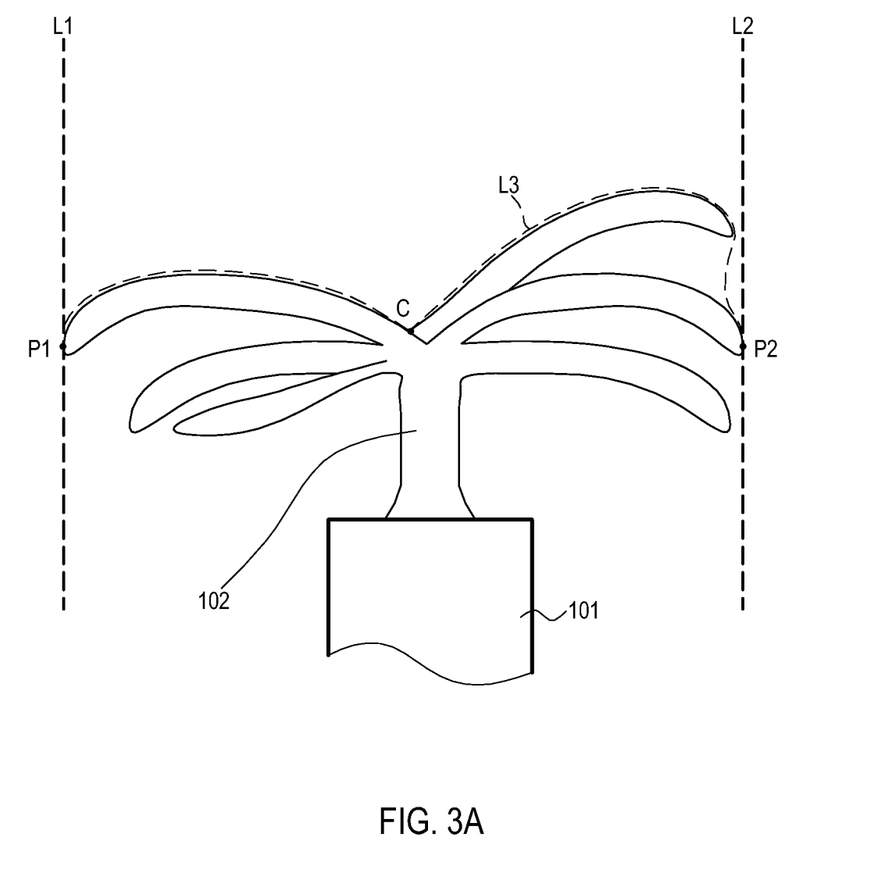
FIG. 3A is a schematic view of an appearance feature image of a plant photographed by a second photographic device of FIG. 1D.

FIG. 3A is a schematic view of an appearance feature image of the plant photographed by the second photographic device of FIG. 1D.

As shown in FIG. 3A, the appearance feature image is the side view image generated by photographing the plant 102 by the second photographic device 22. Here, the image processing module 31 scans the side view image to get the first colorful pixel by using a first vertical scanning line L1 from left side to right side and then from top to bottom, and takes a first point P1 on the first colorful pixel as a first mark. Likewise, starting from the right side, the image processing module 31 scans the side view image from top to bottom for the first colorful pixel by using a second vertical scanning line L2, and takes a second point P2 with the first colorful pixel as a second mark. Then, a line L3 connecting the first point P1 and the second point P2 is used as a function. Next, the image processing module 31 searches for the lowest point of the connecting line L3 being a curve by using a golden section search method, and takes the lowest point as a central point C of the plant 102.

Figure 3B:
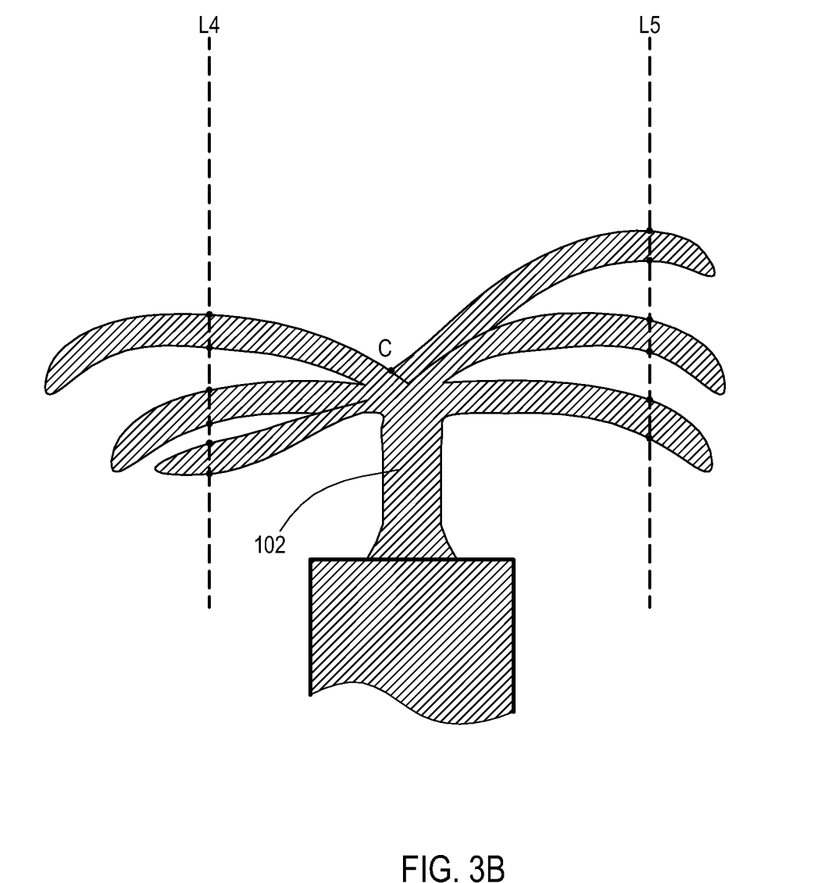
FIG. 3B is a schematic view of the side view image of FIG. 3A after being binarized by an image processing module.

FIG. 3B is a schematic view of the side view image of FIG. 3A after being binarized by the image processing module.

As shown in FIG. 3B, after binarizing the side view image and removing the image noises that are not appearance features of the plant 102, the image processing module 31 firstly searches for the central point C of the plant 102 by using the golden section search method. Through the central point C, the image processing module 31 divides the plant 102 into left and right parts, performs a search analysis on the left part through a vertical line L4, and calculates the number of times that the image on the vertical line L4 changes from black to white and from white to black. In this embodiment, since the image on the vertical line L4 changes from black to white and from white to black for 6 times, it is calculated by dividing 6 by 2 to get the leaf number of the left part of the plant 102, that is 3. By the same calculation method, it is calculated through a vertical line L5 that, in this embodiment, the leaf number of the right part of the plant 102 is also 3.

Figure 4A:
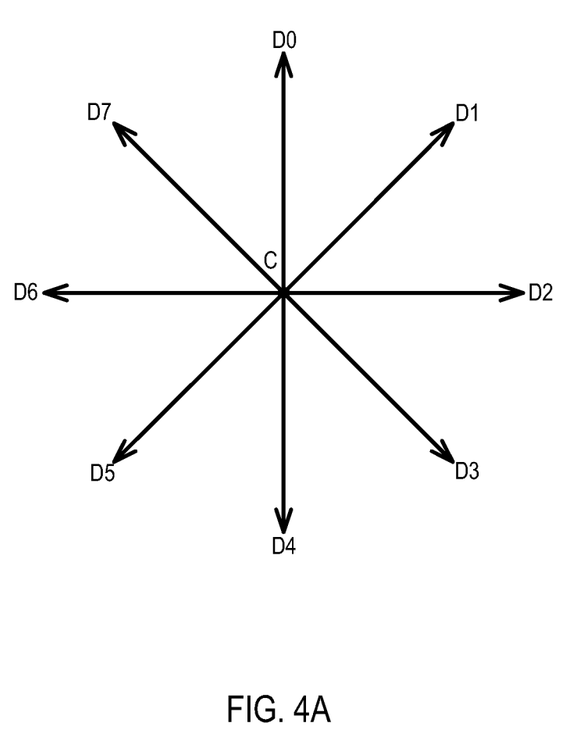
FIG. 4A is a schematic view of a shape description algorithm used by the image processing module of FIG. 1D.
Figure 4B:
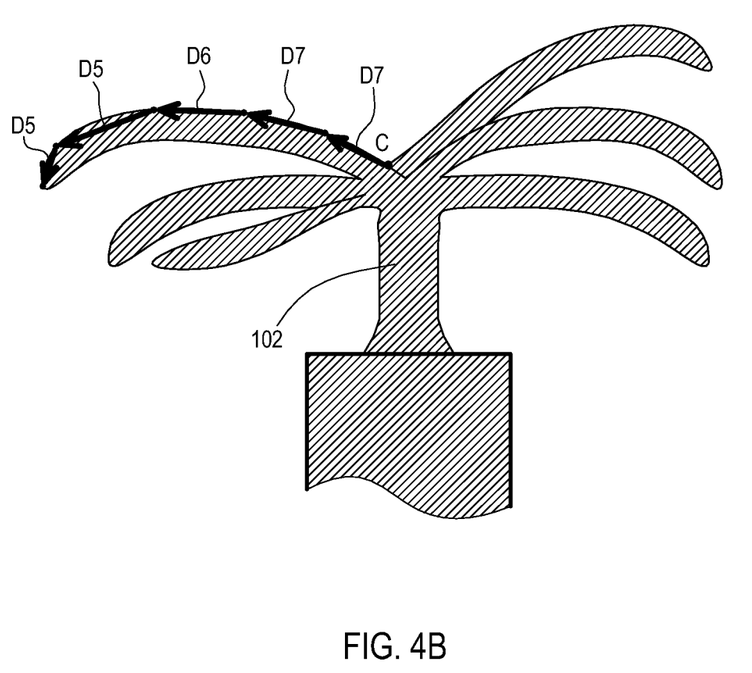
FIG. 4B is a schematic view of an operation that the image processing module calculates a leaf length by using the shape description algorithm according to FIG. 4A.

FIG. 4A is a schematic view of a shape description algorithm used by the image processing module of FIG. 1D, and FIG. 4B is a schematic view of an operation that the image processing module calculates a leaf length by using the shape description algorithm according to FIG. 4A.

As shown in FIG. 4A, after finding the central point C of the plant 102 in the image (for example, the side view image), the image processing module 31 calculates the number of pixels from the central point C to an end point of the leaf by using the shape description algorithm according to directions (for example, directions D0 to D7) from the central point C towards the left part and the right part. Then, the image processing module 31 measures the actual dimension of the plant 102 based on the dimension data of the object with the fixed dimension for comparison that is prestored in the storage unit 32, for example, calculates the actual length corresponding to the pixel number by using a scale (using the container 101 as a standard), so as to obtain actual dimension data of the leaf length of the plant 102, and generate data corresponding to the appearance feature of the plant 102.

For example, as shown in FIG. 4B, after the image processing module 31 finds the central point C of the plant 102 in the image, the image processing module 31 firstly sets a starting direction, for example, the direction D7, from the left part according to the central point C. At this time, the image processing module 31 calculates the pixel number of the left length from the central point C towards the direction D7, the direction D6, and the direction D5 till to the end point of the leaf along the edge of the leaf by using the shape description algorithm. Next, the image processing module 31 measures the actual dimension of the plant 102 based on the dimension data of the object with the fixed dimension for comparison that is prestored in the storage unit 32, for example, calculates the actual length corresponding to the pixel number by using a scale, so as to obtain actual dimension data of the leaf length of the plant 102, and generate data corresponding to the appearance feature of the plant 102. Alternatively, a standard dimension device having a standard dimension marker is directly provided, so as to obtain the actual dimension data of the plant 102 in the container 101 and generate the at least one feature data corresponding to the appearance features of the plant 102 by using the standard dimension marker, the image processing procedure, and the at least one analysis rule.

Figure 5A:
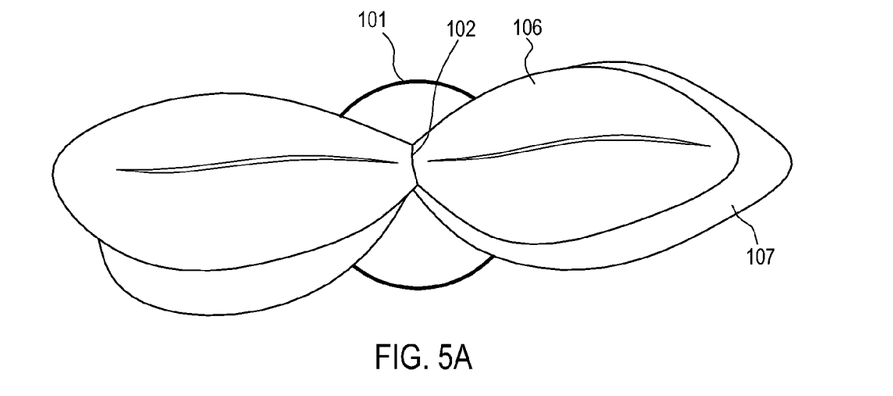
FIG. 5A is a schematic view of the top view image generated by photographing the appearance features of the plant by the first photographic device of FIG. 1D.
Figure 5B:
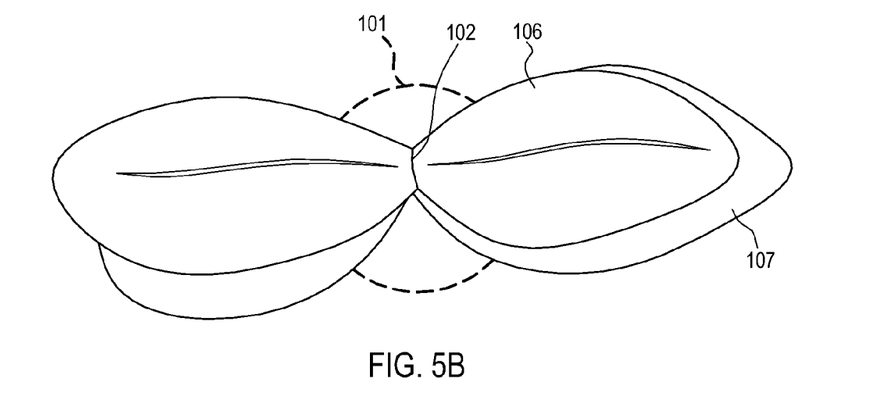
FIG. 5B is a schematic view of an operation for removing an image of the container in FIG. 5A.
Figure 5C:
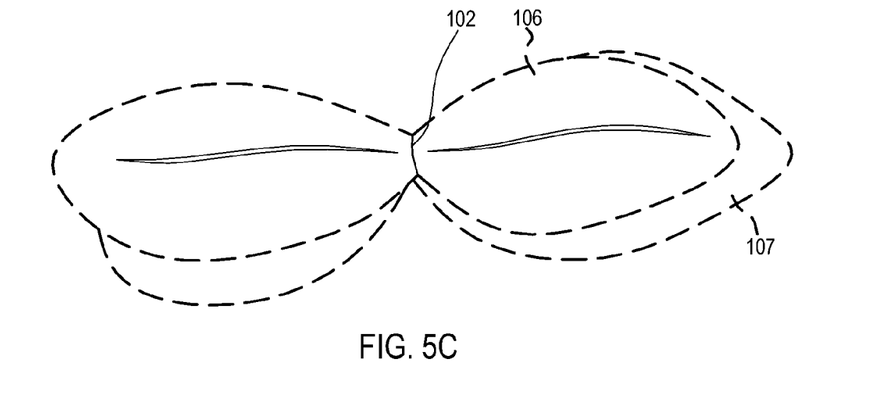
FIG. 5C is a schematic view of the plant image of FIG. 5B after an edge algorithm is performed.
Figure 5D:
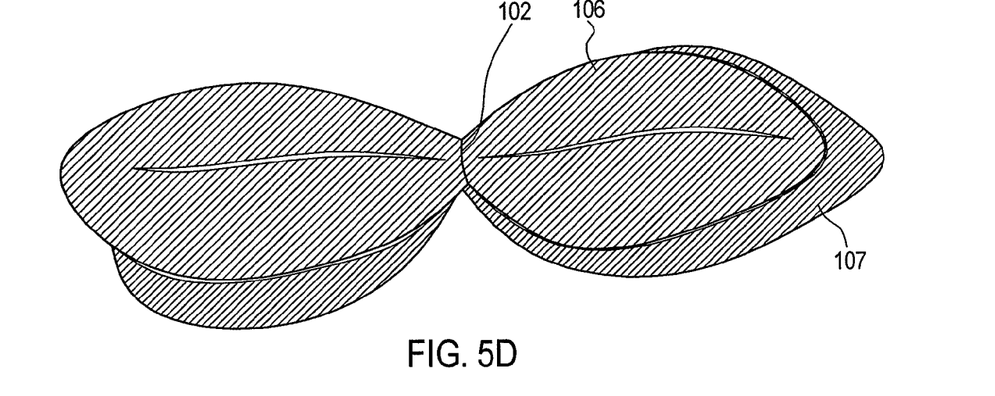
FIG. 5D is a schematic view of the plant image of FIG. 5B after being binarized.
Figure 5E:
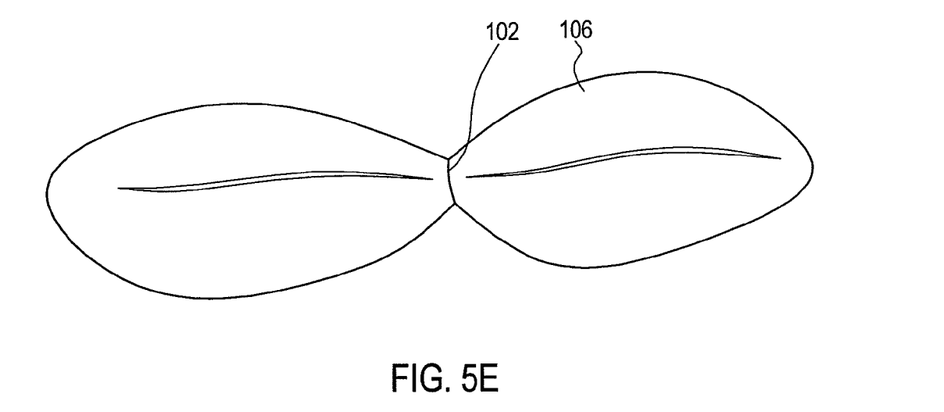
FIG. 5E is a schematic view of the plant images of FIGS. 5C and 5D after an exclusive OR (XOR) operation and a smoothing method are performed.
Figure 5F:
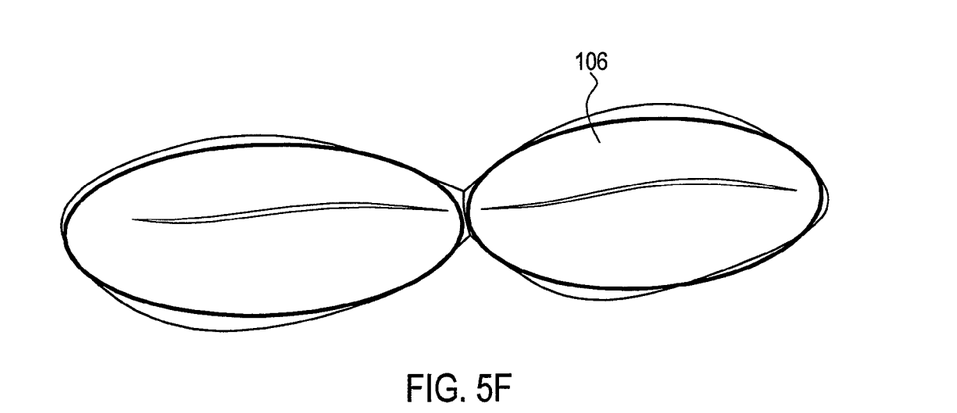
FIG. 5F is a schematic view of the plant image of FIG. 5E after a circle detection algorithm is performed.

FIG. 5A is a schematic view of the top view image generated by photographing the appearance features of the plant by the first photographic device of FIG. 1D, FIG. 5B is a schematic view of an operation for removing an image of the container in FIG. 5A, FIG. 5C is a schematic view of the plant image of FIG. 5B after a edge algorithm is performed, FIG. 5D is a schematic view of the plant image of FIG. 5B after being binarized, FIG. 5E is a schematic view of the plant images of FIGS. 5C and 5D after an XOR operation and a smoothing method are performed, and FIG. 5F is a schematic view of the plant image of FIG. 5E after a circle detection algorithm is performed.

As shown in FIGS. 5A to 5F, the top view image generated by photographing the plant 102 by the first photographic device 21 is shown. In FIGS. 5A to 5F, for description, the width of an upper layer leaf 106 of the plant 102 in the top view image is calculated, but the present invention is not limited thereto.

Firstly, the image processing module 31 firstly removes the image of the container 101 in the top view image by using an R-G layer. Then, the image processing module 31 respectively performs binarization and an edge algorithm (Sobel algorithm) on the top view image obtained after the image of the container 101 is removed. Next, the image processing module 31 performs an XOR operation and a smoothing method on the top view image obtained after binarization and the edge algorithm are performed, such that the upper layer leaf 106 is separated from a lower layer leaf 107 (as shown in FIG. 5E). Afterward, the image processing module 31 performs analysis and calculation along the edge of the leaf by using a circle detection algorithm such as a Hough algorithm in combination with the shape description algorithm used for calculating the leaf length, so as to calculate and identify the width of the upper layer leaf 106. The Hough algorithm is a method for transforming Cartesian coordinates into polar coordinates. When Hough transformation is applied to a circle, the transformed point set is centered at the center of the circle. However, if Hough transformation is applied to a boundary that is not circular, the transformed points are dispersed.

After the leaf length and the leaf width of the plant 102 are obtained by using the above algorithms, the area of the upper layer leaf 106 (approximately elliptical in shape) can be obtained by multiplying the leaf length times the leaf width times an empirical reference value of 0.722. Therefore, the image processing module 31 can calculate feature data of each leaf on the plant 102 in this manner.

Likewise, the image processing module 31 can find out objects like circular images in the top view image or the side view image by using the above circle detection algorithm, and then differentiate the found objects by color. That is to say, based on the fact that different plants have buds of particular colors, the bud number can be calculated. In addition, for the measurement of sprouts of the plant, as time goes on, the image processing module 31 can perform the XOR operation on the top view image or the side view image photographed by the photographic device, so as to directly search for a feature image of sprouts in the image, thereby obtaining the sprout number. The image processing module 31 can calculate the number of pixels from the root to the top of the plant 102 by using the above analysis rule such as the shape description algorithm, and calculate the height of the plant 102 by a scale according to the pixel number. Alternatively the image processing module 31 directly calculates data about angles between the leaves in the image of the plant 102 in the side view image.

Afterward, the image processing module 31 performs the Step S120 of recording the at least one feature data in the storage unit.

In this step, the image processing module 31 stores and records various feature data (at least one selected from a group consisting of the height of the plant, the leaf number, the leaf length of the plant, the leaf width of the plant, the leaf area of the plant, the angle between leaves of the plant, the bud number of the plant, and the sprout number of the plant) generated corresponding to the appearance features of the plant 102 in the storage unit, thereby eliminating the inconvenience of manual recording.

The first photographic device 21 and the second photographic device 22 further respectively photograph the plant 102 in the container 101 at different times and generate the corresponding top view image and side view image, and the at least one analysis rule further includes analyzing the top view image and the side view image corresponding to the different times, so as to generate the at least one feature data corresponding to the appearance features of the plant 102.

The operation processing device 30 further generates the at least one feature data corresponding to the plant 102 in the container 101 at the different times and records the at least one feature data in the storage unit 32. The operation processing device 30 further generates at least one selected from a group consisting of a recording report, a plant growth analysis, and a plant growth history corresponding to the plant 102 in the container 101 according to the at least one feature data corresponding to the plant 102 in the container 101 at the different times by using a plant record processing procedure. The operation processing device 30 further records planting records of the plant 102 in the container 101 at the different times by using the plant record processing procedure, and generates a planting benefit evaluation for the plant 102 in the container 101 according to the planting records of the plant 102 in the container 101 at the different times and the corresponding at least one feature data.

In addition, the automatic measurement method for plant features may also be applied to a recording medium. The recording medium stores a computer program, such that when the computer program is run by an operation processing device, the operation processing device performs the automatic measurement method for plant features described above. The automatic measurement method for plant features is applicable between at least one photographic device and the operation processing device, and the operation processing device at least includes a storage unit. For the method, reference may be made to the above description, so the details will not be described herein again.

It can be known from the above description that, the automatic measurement system for plant features, the automatic measurement method for plant features, and the recording medium according to the present invention has the following advantages.

1. Different from the prior art that the plant features are mostly manually recorded, in the present invention, by applying the at least one photographic device and the operation processing device, the at least one feature data of the appearance features of the plant can be automatically recorded, thereby eliminating the time cost and inconvenience resulting from manual recording.

2. The feature data of the appearance features of the plant is automatically recorded without touching the plant, thereby preventing damages to the plant resulting from direct touching the plant during the manual recording.

3. By photographing the plant in the container and generating the corresponding top view image and side view image, the appearance features of the plant in the container can be analyzed from various angles, thereby obtaining accurate feature data.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An automatic measurement system for plant features, comprising:
   a photographic device, for respectively photographing a plant in a container at different times, so as to generate a top view image and a side view image; and
   an operation processing device, electrically connected to the photographic device, and at least comprising an image processing module and a storage unit, wherein the image processing module analyzes at least one of the top view image and the side view image corresponding to the different times by using an image processing procedure and an analysis rule, so as to generate a feature data corresponding to appearance features of the plant, and records the feature data in the storage unit, and the operation processing device further generates at least one selected from a group consisting of a recording report, a plant growth analysis, and a plant growth history corresponding to the plant in the container according to the feature data corresponding to the plant in the container at the different times by using the plant record processing procedure.

2. The automatic measurement system for plant features according to claim 1, further comprising a case, having a chamber for accommodating the container and the plant, wherein the photographic device for photographing the plant in the container is disposed in the case.

3. The automatic measurement system for plant features according to claim 1, wherein the image processing procedure comprises gray scaling and binarizing at least one of the top view image and the side view image.

4. The automatic measurement system for plant features according to claim 1, wherein the analysis rule comprises at least one selected from a group consisting of a denoising algorithm, an edge algorithm, a shape description algorithm, and a circle detection algorithm.

5. The automatic measurement system for plant features according to claim 1, wherein the feature data comprises at least one selected from a group consisting of a leaf amount, a leaf length, a leaf width, a leaf area, a bud amount, a sprout amount, a height of the plant, and an angle between leaves of the plant.

6. The automatic measurement system for plant features according to claim 1, wherein the operation processing device further records planting records of the plant in the container at the different times by using the plant record processing procedure, and generates a planting benefit evaluation for the plant in the container according to the planting records of the plant in the container at the different times and the corresponding feature data.

7. An automatic measurement method for plant features, applicable between a photographic device and an operation processing device, wherein the operation processing device comprises a storage unit, the method comprising:
   obtaining a top view image and a side view image of a plant in a container, the top view image and the side view image are respectively photographed at different times;
   analyzing at least one of the top view image and the side view image corresponding to the different times by using an image processing procedure and an analysis rule, so as to generate a feature data corresponding to appearance features of the plant; and
   recording the feature data in the storage unit; and
   generating at least one selected from a group consisting of a recording report, a plant growth analysis, and a plant growth history corresponding to the plant in the container according to the feature data corresponding to the plant in the container at the different times by using a plant record processing procedure.

8. The automatic measurement method for plant features according to claim 7, further comprising:
   providing a case, wherein the case has a chamber for accommodating the container and the plant, and the photographic device is disposed in the case so as to photograph the plant in the container.

9. The automatic measurement method for plant features according to claim 7, wherein the image processing procedure comprises gray scaling and binarizing at least one of the top view image and the side view image.

10. The automatic measurement method for plant features according to claim 7, wherein the analysis rule comprises at least one selected from a group consisting of a denoising algorithm, an edge algorithm, a shape description algorithm, and a circle detection algorithm.

11. The automatic measurement method for plant features according to claim 7, wherein the feature data comprises at least one selected from a group consisting of a leaf amount, a leaf length, a leaf width, a leaf area, a bud amount, a sprout amount, a height of the plant, and an angle between leaves of the plant.

12. The automatic measurement method for plant features according to claim 7, further comprising:
   recording planting records of the plant in the container at the different times by using the plant record processing procedure, and generating a planting benefit evaluation for the plant in the container according to the planting records of the plant in the container at the different times and the corresponding feature data.

13. A non-transitory computer-readable recording medium, for storing a computer program, wherein the computer program is readable by an operation processing device to perform an automatic measurement method for plant features, the method is applicable between a photographic device and the operation processing device, the operation processing device comprises a storage unit, and the method comprises:

obtaining a top view image and a side view image of a plant in a container, the top view image and the side view image are respectively photographed at different times;

analyzing at least one of the top view image and the side view image corresponding to the different times by using an image processing procedure and an analysis rule, so as to generate a feature data corresponding to appearance features of the plant;

recording the feature data in the storage unit; and generating at least one selected from a group consisting of a recording report, a plant growth analysis, and a plant growth history corresponding to the plant in the container according to the feature data corresponding to the plant in the container at the different times by using a plant record processing procedure.

14. The non-transitory computer-readable recording medium according to claim 13, wherein the method further comprises:

recording planting records of the plant in the container at the different times by using the plant record processing procedure, and generating a planting benefit evaluation for the plant in the container according to the planting records of the plant in the container at the different times and the corresponding feature data.

* * * * *